United States Patent [19]

Sipinen

[11] Patent Number: 4,985,024
[45] Date of Patent: Jan. 15, 1991

[54] DISPOSABLE DIAPER HAVING FASTENING MEANS THAT ARE DEGRADABLE

[75] Inventor: Alan J. Sipinen, Hugo, Minn.

[73] Assignee: Minnesota Mining and Manufacturing Company, St. Paul, Minn.

[21] Appl. No.: 444,519

[22] Filed: Dec. 1, 1989

[51] Int. Cl.$^5$ .............................................. A61F 13/58
[52] U.S. Cl. ..................................... 604/389; 604/386
[58] Field of Search ....................... 604/386, 389, 391

[56] References Cited

U.S. PATENT DOCUMENTS

| | | | |
|---|---|---|---|
| 4,016,117 | 4/1977 | Griffin | 260/17.4 ST |
| 4,021,338 | 5/1977 | Griffin | 260/13 |
| 4,042,764 | 8/1977 | Gratani et al. | 526/4 |
| 4,133,784 | 1/1979 | Otey et al. | 524/556 X |
| 4,237,889 | 12/1980 | Gobran | 128/287 |
| 4,324,709 | 4/1982 | Griffin | 523/210 |
| 4,337,181 | 6/1982 | Otey et al. | 524/556 X |
| 4,769,283 | 9/1988 | Sipinen et al. | 428/343 |
| 4,793,337 | 12/1988 | Freeman et al. | 128/156 |
| 4,808,474 | 2/1989 | Sipinen | 428/343 |
| 4,810,574 | 3/1989 | Ahner | 604/389 X |
| 4,931,488 | 6/1990 | Chiquet | 524/398 X |

FOREIGN PATENT DOCUMENTS

WO88/09354 12/1988 PCT Int'l Appl. .

Primary Examiner—Randall L. Green
Assistant Examiner—David H. Willse
Attorney, Agent, or Firm—Donald M. Sell; Roger R. Tamte; William J. Bond

[57] ABSTRACT

A disposable diaper can be almost completely degradable when each of its diaper closure tapes has as its backing a polyolefin film containing a chemical prodegradant such as a metal salt together with an unsaturated elastomer such as a block copolymer of styrene and isoprene of butadiene. Preferably, the polyolefin of each of those backings is a copolymer of polypropylene and polyethylene or a blend of crystalline isotatic polypropylene and a compatible ethylene-based polymer.

16 Claims, 1 Drawing Sheet

DISPOSABLE DIAPER HAVING FASTENING MEANS THAT ARE DEGRADABLE

BACKGROUND OF THE INVENTION

1. Field of the Invention

The invention concerns disposable diapers that are degradable and is more specifically concerned with the biodegradability of their diaper-fastening means, namely, the pressure-sensitive adhesive fastening tabs, release tapes, and frontal target strips of such diapers.

2. Background Art

Disposable diapers have employed pressure-sensitive adhesive fastening tabs with paper backings that may be biodegradable. However, paper backings are not reliable unless treated to resist moisture and to afford good strength. Unfortunately, treatments that are effective may inhibit the degradability of the paper. Furthermore, the application of such treatments can make paper expensive. Also, paper is comparatively stiff, so that the tape may not flex with the diaper, and the edge of the tape might injure a baby's tender skin.

Accordingly, paper backings for diaper fastening tabs have been virtually supplanted by fastening tabs having backings of thermoplastic films, see, for example, U.S. Pat. No. 4,237,889 (Gobran). For teachings of making the fastening tabs tougher, see U.S. Pat. No. 4,808,474 (Sipinen); and for teachings of making the tabs soft, pliable, conformable, and heat sealable, see U.S. Pat. No. 4,769,283 (Sipinen et al). The fastening tab of each of these Sipinen patents has a backing of a substantially untensilized, ductile film of a blend of crystalline isotactic polypropylene and a compatible ethylene-based polymer in proportions found to make, e.g., fastening tabs tough or soft, respectively. Useful compatible ethylene-based polymers include an ethylene-propylene polymer and polymers of ethylene-vinyl acetate and ethylene-acrylic acid.

Current interest in disposable diapers has lead to the manufacture of diapers that are claimed to be mostly biodegradable. However, none known has a polyolefin backed degradable fastening tab. Further, tapes used to make fastening tabs are currently not degradable polyolefins. Thus, although the need for degradable fastening tabs, and associated tapes (i.e. frontal target strips and release tapes) exists, a suitable solution is not currently available.

U.S. Pat. No. 4,016,117 (Griffin) imparts biodegradability to a synthetic resin by blending it with natural starch as well as fatty material that apparently serves as a lubricating substance. In Example I, maize starch was blended with ethyl oleate, oleic acid, and low-density polyethylene to form a smooth compound which was diced into cubes that were about 50% by weight starch. The cubes were blended with additional low-density polyethylene to give 8% starch in a composition which was formed into a translucent flexible film that was biodegradable under laboratory conditions designed to simulate a landfill, as reported in Example II. The tensile and tear strengths of this film were only moderately lower than those of identical film except for omission of the starch and fatty material. Other examples of the Griffin patent employ, instead of the low-density polyethylene, polystyrene (Examples III and IV) and polyurethane (Examples XII-XIV). Polypropylene is mentioned at col. 3, line 22. U.S. Pat. No. 4,021,388 (Griffin) contains substantially identical disclosure. U.S. Pat. No. 4,324,709 (Griffin) says that natural starch can be more readily mixed with a polymer by pre-mixing a small amount of a fluid lubricating substance with the starch, e.g. in Example 1, starch was preblended with 10% of ethyloleate, an oily material, together with 4% of calcium stearate, another oily material.

Pellets, used like the cubes of Griffin ,117, are currently marketed as "Polygrade II" by Ampacet Corp., Mt. Vernon, NY. These pellets are based on linear low-density polyethylene and contain 36% by weight starch. The pellets also contain by weight about 0.4% of what is called a chemical prodegradant that is a metal salt plus about 13% by weight of an unsaturated elastomer. Ampacet literature states that these pellets can be blended with either linear or nonlinear low-density polyethylene to produce a film that is biodegradable when its starch content is from about 6 to 12% by weight, and suggests using the film to make garbage bags. The tensile and tear strengths of garbage bags as well as their method of manufacture makes these films unsuitable for use as diaper tapes.

St. Lawrence Starch markets "Ecostar" concentrates in the form of pellets that comprise by weight 52% linear low-density polyethylene, 43% corn starch, and 5% vegetable oil. St. Lawrence Starch also markets "Ecostar Plus" pellets that are believed to be similar to the "Ecostar" pellets except also containing a chemical prodegradant.

Therefore, it is a general object of this invention to solve the problems of the prior art by providing a suitable degradable polyolefin diaper fastening tab.

Summary of the Invention

The invention provides reliable, economical polyolefin diaper-fastening means for disposable diapers that are degradable, hence making it feasible for the first time to manufacture disposable diapers that are almost completely degradable. Degradability of the diaper-fastening means is achieved by employing as the backing of each of the fastening tabs, release tapes, and frontal target strip, which may be used in the particular diaper fastening means, a polyolefin film that contains a chemical prodegradant, such as a metal salt, together with an unsaturated elastomer. The fastening tab can be of any conventional construction and may include target tapes or release tape portions and designed for use with or without a target strip. Generally the polyolefins used have been commercial blends which contain suitable amounts of antioxidants to protect the polyolefin during melt processing.

Preferably, the degradable polyolefin backings of the diaper-fastening means are made from polypropylene, most preferably from a copolymer of polypropylene and polyethylene or from blends of crystalline isotactic polypropylene and a compatible ethylene-based polymer like those of the above-cited Sipinen and Sipinen et al. patents. These polypropylene copolymers and blends provide tapes having superior tape performance characteristics: further, they can be readily blended with a chemical prodegradant and unsaturated elastomer, directly or with a suitable carrier. Preferably, if carriers are used, to incorporate the prodegradant and elastomer, they are chosen to be compatible with the copolymer or blend.

The novel degradable backings can also incorporate a starch, such as corn or rice starch, in amounts up to about 30% by weight of the backing, preferably from 2 to 15%. Starch alone in a polyolefin backing is insufficient to enable such a backing to degrade at a reasonably rapid rate in most landfills, which are sterile. Starch, however, is useful to assist in degradation of the diaper fastening means when the diaper is disposed of in non-sterile surroundings, such as in a compost heap. However, the metal salt and unsaturated elastomer have been found to ensure degradation in both sterile and non-sterile environments.

Diaper-fastening means of the invention have been made with backings having a starch content as high as 36% by weight of the backing. However, at that high proportion of starch, a backing tends to be undesirably weak for any tape used in the fastening means, even in a release tape backing for which strength is not as important. Release tapes protect the adhesive fastening tape prior to use. For release tape backings the proportion of starch preferably does not exceed 30%. When the fastening means is a diaper fastening tab, which requires greater strength and toughness (measured here as tear strength), the proportion of starch preferably does not exceed 20% by weight. The backing of a frontal target strip needs to be somewhat tougher than that of a release tape but not as tough as a fastening tab, so preferably it can comprise up to about 25% starch by weight.

The minimum acceptable tear strength for fastening tabs, frontal strips and release tapes is generally at least about 100, 70 and 40 grams/ply, respectively, and preferably at least 120, 90 and 60 grams/ply, respectively. Strength is not as critical for the tapes of the diaper-fastening means. However, generally a tensile strength of about at least 120 Kgs/cm$^2$ in the cross direction is required for an acceptable tape performance. As such for a tape to be suitable for use as a diaper-fastening means of the invention its tear strength should generally be at least 40 grams/ply while its tensile strength generally should be at least 120 Kgs/cm$^2$:

When starch is incorporated into a polyolefin film, processing of the polyolefin becomes more difficult, but this can be offset in part by employing either a copolymer of polypropylene and polyethylene or a blend of the above-cited Sipinen and Sipinen et al patents. Processing can be further enhanced by the use of a processing aid such as a fluoroelastomer.

Preferably when used as the prodegradant the metal salt is employed in amounts such that the metal comprises from 0.001 to 1.0% by weight of the novel backings. At substantially larger amounts, the backing might excessively degrade under ordinary storage conditions, whereas degradation would be undesirably slow if smaller amounts were used. Suitable metal salts include, for example, transition metal salts of Ce, Zn, Cu, Ag, Ni, Co, Fe, Mn, Cr and V and organic acids such as stearates, oleates, behenates, myristates, erucates, linoleates, or naphthenates. Complexes can also be used.

Preferably the unsaturated elastomer is employed in amounts from 0.25 to 30% by weight of the novel backings. At substantially larger amounts, the backing would not have sufficient tensile strength and modulus. At substantially smaller amounts, degradation has been found to be unduly slow with preferred amounts of metal salt. Typical suitable unsaturated elastomers include natural rubber and A-B or A-B-A block copolymers, such as styrene-isoprene or styrene-butadiene block copolymers.

DETAILED DESCRIPTION

Figure 1:
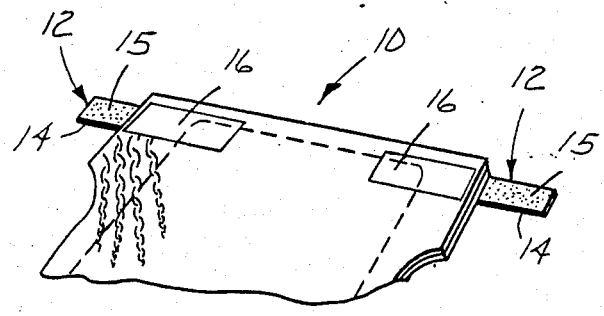

Pressure-sensitive adhesives that are based on unsaturated elastomers gradually degrade and do so more quickly at moderately elevated temperatures. Such adhesives are preferred to adhere the novel fastening tabs, release tapes, and frontal target strip to the outer shell of the disposable diaper, and also as the fastening adhesive of the fastening tabs. When the outer shell is polyethylene film, each of the frontal target strips and release tapes can instead be heat-sealed directly to the outer shell or adhered thereto using a heat- or solvent-activated adhesive.

Preferred degradable pressure-sensitive adhesives are those which are based on a blend of natural rubber or an elastomeric block copolymer with one or more tackifying resins and plasticizers. Especially preferred are blends of an elastomeric block copolymer with a plasticizing oil such as naphthenic oil and a tackifying resin such as a solid hydrocarbon resin.

The actual tackifiers and plasticizers used are not important as long as they are compatible with the natural rubber or elastomeric block copolymer. The tackifying resin preferably comprises a blend of a solid tackifying resin and a liquid tackifying resin, a single solid tackifying resin, or a blend of a solid tackifying resin and a liquid plasticizer. Tackifying resins include those aliphatic hydrocarbon resins made from the polymerization of a feed stream consisting mainly of unsaturated species containing four to six carbon atoms, such as "Wingtack Plus" and "Wingtack" 95 from Goodyear Tire and Rubber Co., "Escorez" 1310 from Exxon Chemical Co., and "Hercotac" RT-95 from Hercules, Inc.; and rosin esters and rosin acids such as "Hercoflex" 400, "Regalite" 355 and "Permalyn" 305 from Hercules, Inc.; mixed aliphatic/aromatic tackifiers such as "Escorez" 2520 polyterpene tackifiers such as "Zonarez" A-25 from Arizona Chemical Co. and hydrogenated tackifying resins. Preferred liquid plasticizers include naphthenic oils such as "Shellflex" 371 from Shell Chemical Co., paraffinic oils, aromatic oils, and mineral oils such as "Kaydol" oil from Witco Chemical Corp.

The exposed face of each of the frontal target strip and release tapes preferably has a low-adhesion backsize (LAB) coating to permit the fastening tabs to be removed and refastened. Preferred is a urethane-type LAB formed by the reaction of an ethylene/vinyl alcohol copolymer with octadecyl isocyanate.

THE DRAWING

Figure 2:
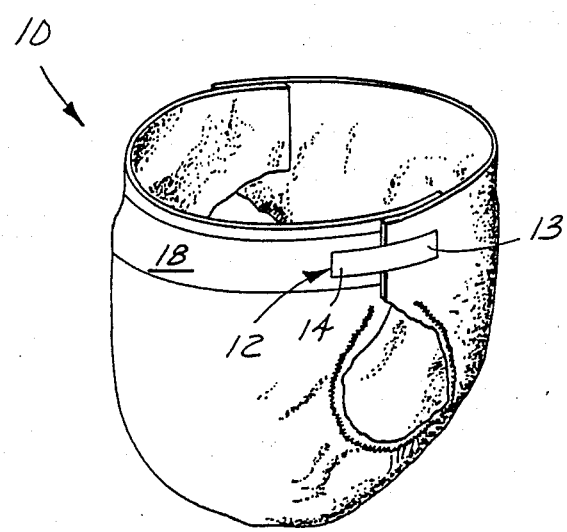

The invention may be more easily understood in reference to the drawing in which:

FIG. 1 is a fragmentary schematic perspective view of a disposable diaper having degradable diaper-fastening means, namely, pressure-sensitive adhesive fastening tabs, release tapes, and a frontal target strip, with one of the fastening tabs open; and FIG. 2 is a schematic perspective view of the diaper of FIG. 1 as it would appear while being worn.

In the drawing, a disposable diaper 10 has a pair of fastening tabs 12, each having a flexible backing, one end 13 of which is adhered to the body of the diaper by a pressure-sensitive adhesive (not shown). The free end 14 of each fastening tab bears a fastening layer of pressure-sensitive adhesive 15. As packaged, the fastening adhesive layer of each of the fastening tabs is protected by one of a pair of release tapes 16, each of which has a backing that is adhered to the diaper by a layer of pressure-sensitive adhesive (not shown). Across the front of the diaper, a frontal target strip 18 has been adhered to the diaper by its layer of pressure-sensitive adhesive (not shown).

TESTING

In the examples, tensile strength was measured using ASTM D-882-81. When testing an adhesive tape, the tensile strength is based on the cross-sectional area of the backing.

TEAR RESISTANCE

Tear Resistance can be measured using an Elmendorf ™ Tear Tester. In this test a 7.5 cm long by 6.3 cm wide tape sample is mounted between a pair of fixed vertical clamps with a spacing of 2.5 mm between the clamps. A 20 mm starter slit is cut in the lower edge of the tape between the clamps. A pendulum is released that tears the tape between the clamps. The pendulum carries a pointer that indicates the tear strength of the tape. The measurement is in the machine (downweb) direction of the tape.

90° PEEL VALUE

This is a 90° peel from a smooth polyethylene substrate at 12 inches (30 cm) per minute. The test samples are rolled down onto the polyethylene substrate using two passes of a 2 kg. roller. This test is a variation on PSTC-5.

SHEAR VALUE

This test employs a polyethylene substrate, namely an embossed material found on LUV ™ brand disposable diapers manufactured by Procter and Gamble which is about 30.5 μm thick. To enhance its stiffness, the polyethylene substrate is laminated to a pressure-sensitive tape. On the side opposite the stiffening tape, a one inch (2.54 cm) square area of the test tab tape is rolled down onto the polyethylene substrate using two passes of a hard rubber (2.2 kg) roll. The laminated substrate and test tab tape are hung vertically in a 40° C. oven, and a 500 gram weight is hung from the test tab tape. The time for the weight to drop is reported as "Shear Creep Resistance". The test is discontinued when there has been no failure after 1000 minutes.

| Trade Name | Composition | Source |
|---|---|---|
| "Dypro" 8771 | Polypropylene (melt flow index of 9) | Fina Oil & Chemical |
| "Dypro" 3576 | Polypropylene (melt flow index of 9) | Fina Oil & Chemical |
| "Shell" 7C50 | Ethylene/propylene impact copolymer (8:92, MFI 8) | Shell Chemical Co. |
| "Shell" 7C04N | Ethylene/propylene impact copolymer (8:92, MFI 35) | Shell Chemical Co. |
| "Shell" 5A95 | Polypropylene (Melt Flow Index of 9) | Shell Chemical Co. |
| "Poly Grade" II (20835F) | Polypropylene/starch blend (51:36) containing 13% unsaturated elastomer and 0.4% metal salt. | Ampacet Corp. |
| "Poly Grade" II (20079F) | 7C04N impact copolymer/ unsaturated elastomer blend (72:28) | Ampacet Corp. |
| "Poly Grade" II (20066F) | 7C04N impact copolymer/ metal salt blend (88:12) | Ampacet Corp. |
| CBE 101P | 50% TiO$_2$ in polypropylene (MFI 35) | C. B. Edwards Co. |

EXAMPLES 1–13

Dry blends as indicated in Table I were extruded in an extruder having a 6.25-cm diameter screw with a 30/1 length/diameter ratio. Each of the extruder films was cast into a nip incorporating a rubber-covered roll that has a coarse matte surface and a water-cooled metal roll that has a finish as described here.

When extruding the films of Examples 1–6, 11, 12 and 13, the metal roll had a course matte surface that afforded a coarse matte finish on the face of the film (called "Surface Finish A" in Table I) When extruding the films of Examples 7 and 8, the metal roll had a smooth shiny finish that afforded a smooth shiny film called "Surface Finish C" in Table I. When extruding the films of Examples 9 and 10, the metal had a fine matte finish that afforded a fine matte finish film (called "Surface Finish BB" in Table I). Examples 1, 2, 5, 7, 9 and 12 are comparative examples. Example 1 is a pure polypropylene tab. Examples 2 and 7 are polypropylenes with white pigment. Example 5 is a copolymer with pigment. Example 9 is a copolymer alone. Example 12 is a second polypropylene polymer alone.

Table I also indicates the use to which each of the tapes was put:

D = Fastening tab backing
E = Release tape backing
F = Frontal target strip backing

TABLE I

| Example | C1 | C2 | 3 | 4 | C5 | 6 | C7 | 8 | C9 | 10 | 11 | C12 | 13 |
|---|---|---|---|---|---|---|---|---|---|---|---|---|---|
| Dypro ™ 3576 | 100 | 95 | 85 | 80 | | | 95 | 80 | | | 65 | | |
| Dypro ™ 8771 | | | | | | | | | | | | | |
| Shell ™ 7C50 | | | | | 95 | 80 | | | | | | | |
| Shell ™ 7C04N | | | | | | | | | 100 | 85 | | | |
| Shell ™ 5A95 | | | | | | | | | | | | 100 | 95.6 |
| Poly-Grade II ™ | | | | | | | | | | | | | |
| (20835F) | | | 15 | 15 | | 15 | | 15 | | 15 | 30 | | |
| (20079F) | | | | | | | | | | | | | 3.0 |
| (20066F) | | | | | | | | | | | | | 1.4 |
| CBE101P | | 5 | | 5 | 5 | 5 | 5 | 5 | | | 5 | | |
| Roll Contact Time (sec.) | 0.79 | 0.79 | 0.79 | 0.79 | 0.79 | 0.79 | 0.79 | 0.79 | 0.79 | 0.79 | 0.79 | 0.47 | 0.47 |
| Melt Temp. (°C.) | 229 | 228 | 229 | 224 | 227 | 227 | 221 | 221 | 201 | 208 | 226 | 231 | 231 |
| Roll Temp. (°C.) | 10 | 10 | 10 | 16 | 11 | 11 | 38 | 38 | 38 | 38 | 16 | 10 | 10 |

TABLE I-continued

| Example | C1 | C2 | 3 | 4 | C5 | 6 | C7 | 8 | C9 | 10 | 11 | C12 | 13 |
|---|---|---|---|---|---|---|---|---|---|---|---|---|---|
| Basis Wgt. (g/m$^2$) | 94 | 94 | 94 | 94 | 109 | 109 | 77 | 77 | 52 | 52 | 94 | 94 | 94 |
| Surface Finish | A | A | A | A | A | A | C | C | B | B | A | A | A |
| USE | D | D | D | D | D | D | E | E | F | F | D | D | D |

PRESSURE-SENSITIVE ADHESIVE TAPES

The film of each of Examples 1–13 was coated with a (50%) solution (a toluene/heptane 80:20 mixture) of a degradable pressure-sensitive adhesive. Three adhesives were employed (here called PSAs X, Y and Z). PSA Z was coated from hot melt without solvent.

Compositions of the three PSAs are reported in Table II.

TABLE II

| PSA | X | Y | Z |
|---|---|---|---|
| Kraton ™ 1111 | 44.6 | 35.6 | 37.0 |
| Wingtack ™ Plus | 47.3 | 51.9 | 50.0 |
| Shellflex ™ 371 | 7.1 | 11.5 | 13.0 |
| Irganox ™ 1076 | 1.0 | 1.0 | 0.0 |

Kraton ™ 1111, styrene-isoprene-styrene block copolymer from Shell Chemical.
Wingtack ™ Plus, solid hydrocarbon tactifying resin from Goodyear Chemical.
Shellflex ™ 371, naphthenic oil from Shell Chemical.
Irganox ™ 1076 antioxidant from Ciba-Geigy.

These tapes were tested as reported in Table III.

TABLE III

| Backing of Example | C1 | C2 | 3 | 4 | C5 | 6 | C7 | 8 | C9 | 10 | 11 | C12 | 13 |
|---|---|---|---|---|---|---|---|---|---|---|---|---|---|
| Adhesive Type | X | Y | X | Y | N | X | Y | Y | Z | Z | Y | N | N |
| Coating Wgt. (mg/cm$^2$) | 3.6 | 3.8 | 3.7 | 4.6 |  | 3.4 | 4.6 | 4.3 | 2.1 | 2.1 | 3.3 |  |  |
| Tensile strength of backing in CD (Kg/cm$^2$) | 219 | 202 | 201 | 206 | 139 | 158 | 253 | 233 | 202 | 181 | 164 | 215 | 219 |
| Tear strength in MD (grams/ply) | 200 | 184 | 102 | 126 | 454 | 556 | 152 | 59 | 126 | 145 | 84 | 208 | 186 |
| 90° Peel Value (N/cm) | 3.4 | 3.8 | 3.5 | 3.8 |  | 3.6 |  |  | 3.6 | 3.8 | 3.4 |  |  |
| Shear Value (min.) | 1160 | 220 | 1020 | 240 |  | 720 | 130 | 90 | 250 | 390 | 260 |  |  |

Although the degradable polypropylene tape of Example 3 has significantly lower tear strength than the comparative Example 1 tape, this value is still acceptable for use in a diaper tape. The addition of the degradation system components did not significantly affect the tensile strength, peel value or shear value of the tape, which is true also for Example 4, as compared to comparative Example 2.

Example 6 demonstrates significant tear strength improvement of the degradable copolymer tape over both the degradable and non-degradable polypropylene tapes of Examples 3 and 1, respectively, although the tape basis weight is not that much higher. A very remarkable feature of Example 6 is that the additive increased rather than decreased the tear and tensile strength, rather than decreased these values, when compared to comparative Example 5. This increase in tear strength was also noticed in Example 10 as compared to comparative Example 9.

Example 8 also demonstrates the effect of Roll Temperature. With a higher Roll Temperature crystallinity will increase, increasing the tensile strength, however decreasing the tear strength, which is not as critical for release tapes or target strips.

Example 11 demonstrates the effect of an overall increase in the degradant components as decreasing the tensile and tear strength as compared to Example 4.

Example 13 demonstrates the use of the chemical degradant alone without starch, which produced tapes with superior tear and tensile strengths as compared to the starch loaded Examples 3 and 4.

Examples 11 is a tape prepared for use as a fastening tab but had too low of a tear strength to be useful as such. If the most preferred copolymer was used instead of polypropylene it would be expected that this amount of starch loading (i.e., 30 weight percent of Polygrade ™ II 20835F) could be achieved.

In addition to being useful as fastening tabs, release tapes, and frontal target strips of disposable diapers, degradable tapes of the invention should be useful in other items, e.g., surgical gowns and other disposable garments.

The above examples are merely illustrations of presently preferred embodiments for carrying out the invention and are only exemplary, with the true scope and spirit of the invention being indicated by the following claims.

What is claimed is:

1. A disposable diaper having diaper-fastening means comprising at least one member from the group of fastening tabs, release tapes and a frontal strip, which incorporates a degradable film backing comprising a polyolefin film containing a chemical prodegradant and an unsaturated elastomer wherein said film backing has sufficient tensile and tear strengths for use in a disposable diaper.

2. A disposable diaper as defined in claim 1 wherein said polyolefin film comprises a blend of crystalline isotactic polypropylene and a compatible ethylene-based polymer.

3. A disposable diaper as defined in claim 1 wherein said polyolefin film comprises a copolymer of polypropylene and polyethylene.

4. A disposable diaper as defined in claim 1 wherein said chemical prodegradant is a metal salt.

5. A disposable diaper as defined in claim 4 wherein the metal of said metal salt comprises from 0.001 to 1.0% by weight of said backing.

6. A disposable diaper as defined in claim 1 wherein said unsaturated elastomer is selected from styrene/isoprene or styrene/butadiene block copolymers and natural rubber.

7. A disposable diaper as defined in claim 6 wherein said unsaturated elastomer comprises from 0.25 to 30% by weight of said backing.

8. A disposable diaper as defined in claim 1 wherein said polyolefin film further comprises from up to by weight of natural starch.

9. A disposable diaper as defined in claim 1 wherein the backing of said diaper-fastening means bears a layer of degradable pressure-sensitive adhesive by which the diaper-fastening means is secured to the body of the diaper.

10. A disposable diaper as defined in claim 9 wherein said degradable pressure-sensitive adhesive is based on a blend of natural rubber or a block copolymer with one or more tackifying resins and plasticizers.

11. A disposable diaper as defined in claim 1 wherein said polyolefin film comprises a polypropylene.

12. A disposable diaper as defined in claim 5 wherein said metal salt is a transition metal salt.

13. A disposable diaper as defined in claim 1 wherein the tear strength of the film is at least 40 grams/ply.

14. A disposable diaper as defined in claim 1 wherein said diaper-fastening means comprises a release tape, and wherein the tear strength of the film is at least 40 grams/ply.

15. A disposable diaper as defined in claim 1 wherein said diaper-fastening means comprises a release tape, and wherein the tear strength of the film is at least 70 grams/ply.

16. A disposable diaper as defined in claim 1 wherein said diaper-fastening means comprises a release tape, and wherein the tear strength of the film is at least 100 grams/ply.

* * * * *

UNITED STATES PATENT AND TRADEMARK OFFICE
CERTIFICATE OF CORRECTION

PATENT NO. : 4,985,024

DATED : January 15, 1991

INVENTOR(S) : Alan J. Sipinen

It is certified that error appears in the above-identified patent and that said Letters Patent is hereby corrected as shown below:

On the title page:
Abstract, line 6, after the word "isoprene", delete the word "of" and insert therefor --or--.

Column 2, line 6, delete ",117," and insert therefor --'117,--.

Column 5, lines 47 and 48, add a new paragraph before the chart that reads:

--Used in the examples to make degradable backings were the following:--

Column 6, line 28, delete the word "extruder" and insert therefor --extruded--.

Column 6, line 31, delete the word "has" and insert therefor --had--.

Column 9, line 12, after the word "to" and before the word "by", insert --30%--.

Signed and Sealed this

Twenty-eighth Day of July, 1992

Attest:

DOUGLAS B. COMER

Attesting Officer

Acting Commissioner of Patents and Trademarks